(12) United States Patent
Jones

(10) Patent No.: US 10,470,832 B1
(45) Date of Patent: Nov. 12, 2019

(54) HYGIENIC GLOVE WITH INTEGRAL REMOVAL ENGAGEMENT TABS

(71) Applicant: Stephen E. Jones, Poland, OH (US)

(72) Inventor: Stephen E. Jones, Poland, OH (US)

( * ) Notice: Subject to any disclaimer, the term of this patent is extended or adjusted under 35 U.S.C. 154(b) by 393 days.

(21) Appl. No.: 15/617,356

(22) Filed: Jun. 8, 2017

(51) Int. Cl.
*A41D 19/00* (2006.01)
*A61B 42/10* (2016.01)
*A41D 19/04* (2006.01)

(52) U.S. Cl.
CPC .......... *A61B 42/10* (2016.02); *A41D 19/0003* (2013.01); *A41D 19/0082* (2013.01); *A41D 19/04* (2013.01); *A41D 2400/70* (2013.01)

(58) Field of Classification Search
CPC ................ A41D 2400/70; A41D 19/04; A41D 19/0003; A41D 19/0082; A61B 42/50; A61B 42/10
See application file for complete search history.

(56) References Cited

U.S. PATENT DOCUMENTS

| 4,876,747 | A | | 10/1989 | Coffey et al. | |
|---|---|---|---|---|---|
| 5,365,608 | A | * | 11/1994 | Flick | A41D 19/0003 2/161.7 |
| 5,467,483 | A | | 11/1995 | Saadatmanesh et al. | |
| 5,566,394 | A | * | 10/1996 | Flick | A41D 19/0003 2/161.7 |
| 5,579,539 | A | * | 12/1996 | Flick | A41D 19/0003 2/161.7 |
| 7,624,455 | B1 | | 12/2009 | Bhalla | |
| 2007/0061942 | A1 | * | 3/2007 | Schrodl | A41D 19/0082 2/159 |
| 2013/0067638 | A1 | | 3/2013 | Patkov | |
| 2015/0257835 | A1 | | 9/2015 | Le Blanc | |
| 2016/0227851 | A1 | | 8/2016 | Le Blanc | |
| 2017/0318879 | A1 | * | 11/2017 | Gleser | A41D 19/0093 |

* cited by examiner

*Primary Examiner* — Anna K Kinsaul
(74) *Attorney, Agent, or Firm* — Harpman & Harpman

(57) ABSTRACT

An elastomeric glove having formed integral removal engagement finger tabs for gripping removal without exposing wearer to contaminated glove surfaces. Engagement finger tabs are formed within the glove defining raised exterior surface engagement bands when grasped for assured grasping grip for proper safe glove removal in accordance with accepted glove removal standards.

8 Claims, 5 Drawing Sheets

HYGIENIC GLOVE WITH INTEGRAL REMOVAL ENGAGEMENT TABS

BACKGROUND OF THE INVENTION

1. Technical Field

This invention relates to disposable gloves, specifically the safe removal of gloves used in medical healthcare and food preparation fields to prevent cross contamination after use which may occur during removal.

The use and subsequent safe removal of form fitting elastomeric gloves used in healthcare and food preparation fields requires the user to avoid touching any part of their skin such as the wrist during removal which is very difficult. Given the number and variety of situations, the use of the gloves has become ubiquitous and therefore removal almost a secondary automatic action.

To aid in the safe removal, guidelines for use of glove and removal have been developed that if followed will reduce the possibility of cross contamination which may occur during automatic haphazard removal.

The guidelines require the pinching of the glove surface inwardly from its termination access point on the wrist and peeling away the body of the glove inside out from the user's hand. The pinching and gripping of the flat, smooth glove surface is often difficult and may require several tries and if the grip is lost, the glove material may snap back against the user's hand increasing the chance of cross contamination to others by splattering contaminants to skin, face, clothing or equipment.

2. Description of Prior Art

Prior art gloves have been developed to aid in the safe and preferred approved guidelines for glove sequential removal, see for example U.S. Pat. Nos. 4,876,747, 5,467,483, 7,624,455 and U.S. Patent Publications 2013/0067638, 2015/0257835, and 2016/0227851.

In U.S. Pat. No. 4,876,747, a glove is disclosed with removal means having a raised loop attached to the wrist portion of a glove.

U.S. Pat. No. 5,467,483 is directed to a surgical glove with a removal tab concealed under a cover tab attached to the outside of the glove that is removed exposing the engagement tab for use.

U.S. Pat. No. 7,624,455 illustrates a sterile glove with a touchless donning. The glove has a cuff folded over with a detachable tab used to facilitate cleaning before being detached.

U.S. Patent Publication 2013/0067638 claims a protective glove having a multiple layer construction with a tab extending downwardly from the glove's respective opening.

Patent Publication 2015/0257835 shows a glove with a removable tab extending from the glove access opening as an attachment or being integral with the glove.

Finally, U.S. Patent Publication 2016/0227851 discloses a sterile tab for glove removal. The tab extends from the bottom open edge with an inner end border.

SUMMARY OF THE INVENTION

A glove that can prevent contamination when being removed having a pair of opposing foreshortened finger tabs that extend from the glove surface. Each finger tab, when engaged, selectively locks its intermediate interior surface together, thus defining a plurality of enhanced user engagement gripping surfaces on the exterior of the tab. Each tab is spaced inwardly from the glove's access opening providing proper engagement orientation of the tab to facilitate the safe removal of the glove.

DETAILED DESCRIPTION OF THE INVENTION

Figure 1:
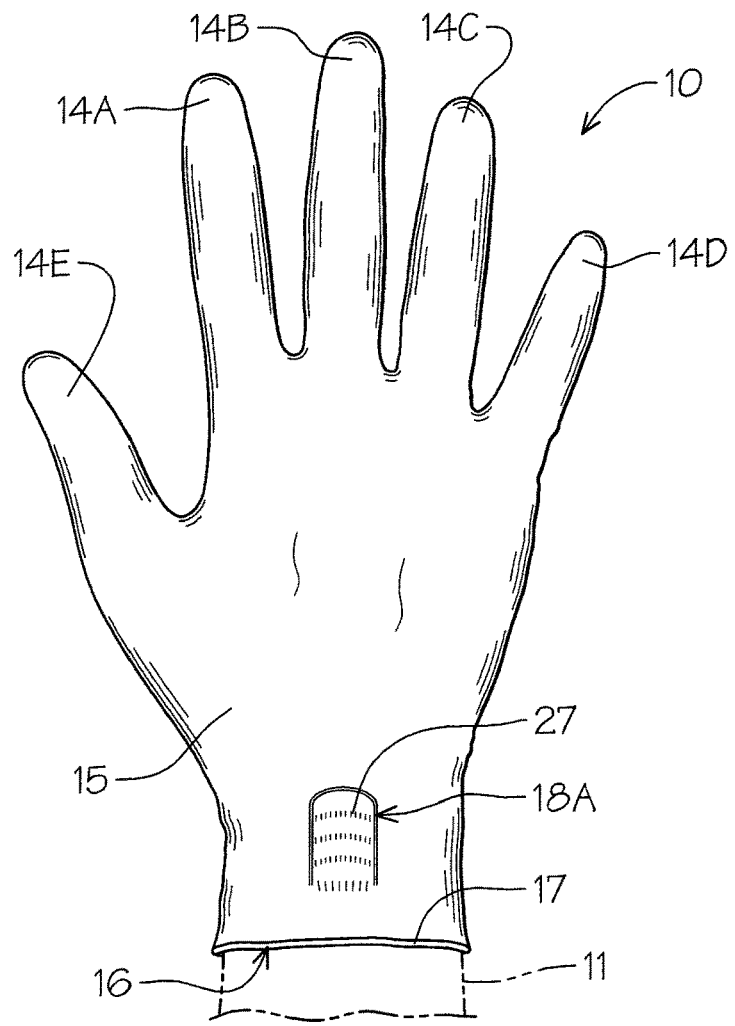
FIG. 1 is a front elevational view of the glove of the invention with a finger engagement tab extending therefrom.
Figure 2:
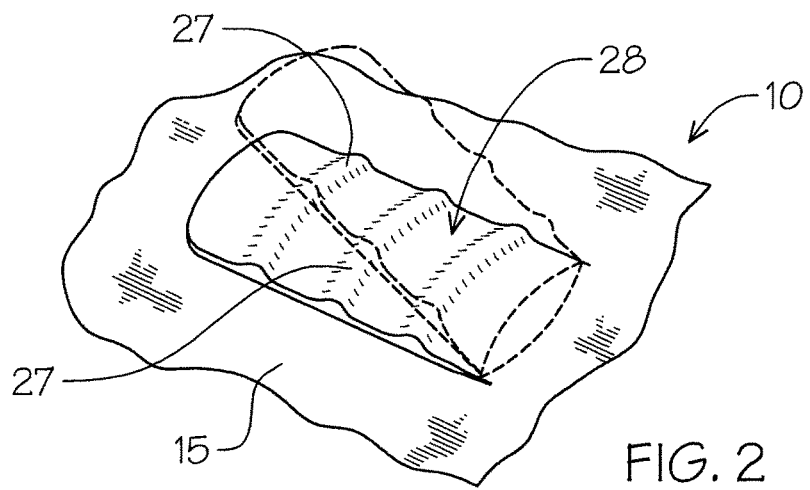
FIG. 2 is an enlarged partial perspective view of the finger tab in non-use position in solid lines and an elevated engagement use position shown in broken lines.

Referring to FIGS. 1 and 2 of the drawings, a glove 10 of the invention can be seen on a human hand 11 shown in broken lines. The glove 10 includes a hand body member 12 with a plurality of finger enclosures 14A, 14B, 14C, and 14D and a thumb enclosure 14E extending in communication with the hand portion 12. A wrist portion 15 extends therefrom with an opening access 16 having a rolled perimeter edge lip 17 thereabout.

Figure 3:
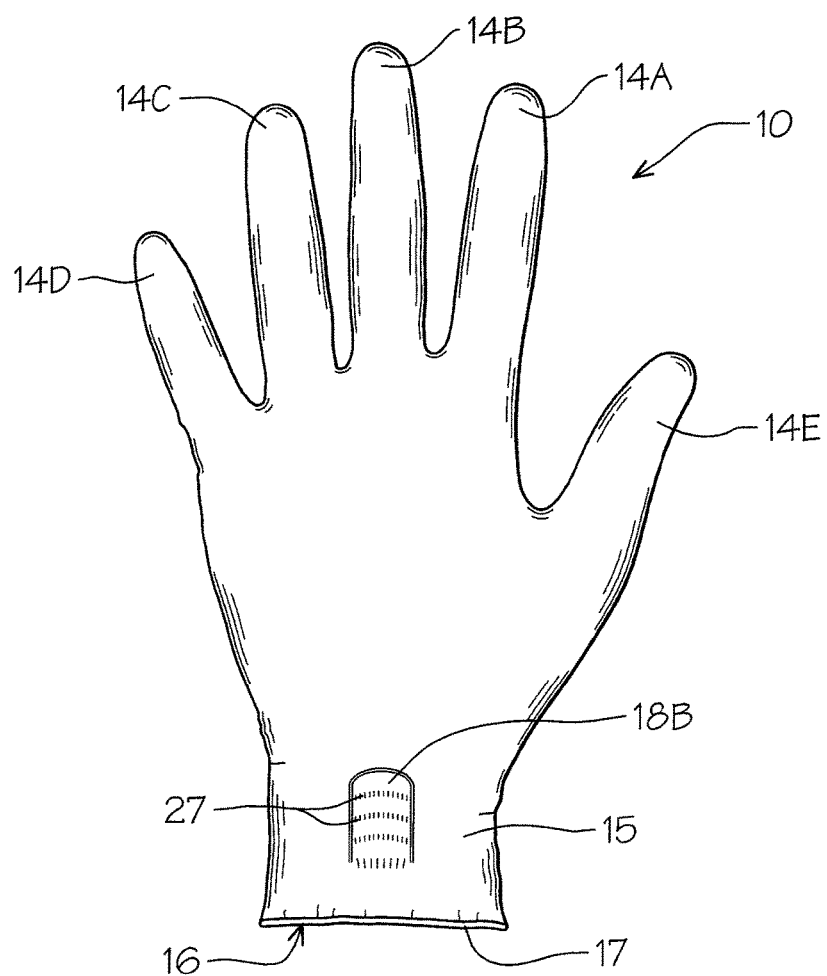
FIG. 3 is a rear elevational view of the glove of the invention with a second finger tab extending therefrom.

A pair of finger tabs 18A and 18B to facilitate the safe removal of the glove are formed on the wrist portion 15 in oppositely disposed relation inwardly from the hereinbefore defined glove open access 16 and its perimeter edge lip 17 as best seen in FIGS. 1-3 of the drawings providing for an ambidextrous glove use orientation as is found in the medical field glove's environment.

The glove is formed of thin elastomeric synthetic resin material by conventional means on a hand mold. A conventional medical glove manufacturing technique forms thin flexible medical gloves with multiple finger openings over a hand mold which lends itself to the adaptation required to form the glove 10 of the invention.

A modified hand glove mold 19 of the invention can be seen in FIGS. 10 and 11 of the drawings as an addition of extra finger-like mold representations 19A and 19B of a reduced longitudinal length and transverse axial dimension as will be described in greater detail hereinafter positioned on oppositely disposed orientation to one another on the mold's wrist portion 20.

Figure 8:
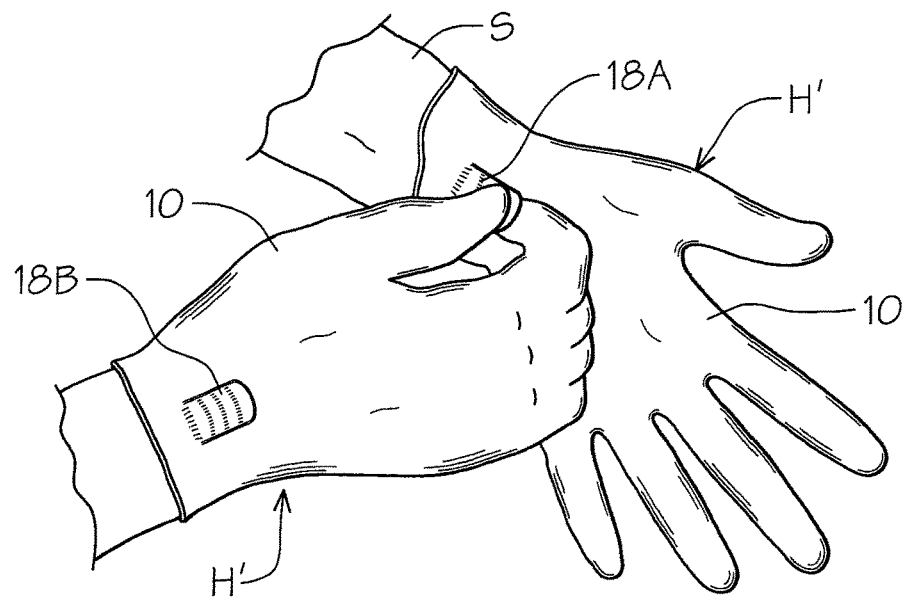
FIG. 8 is an illustration of the glove's removal engagement by the initial engagement of the finger tabs by the user's other hand.
Figure 9:
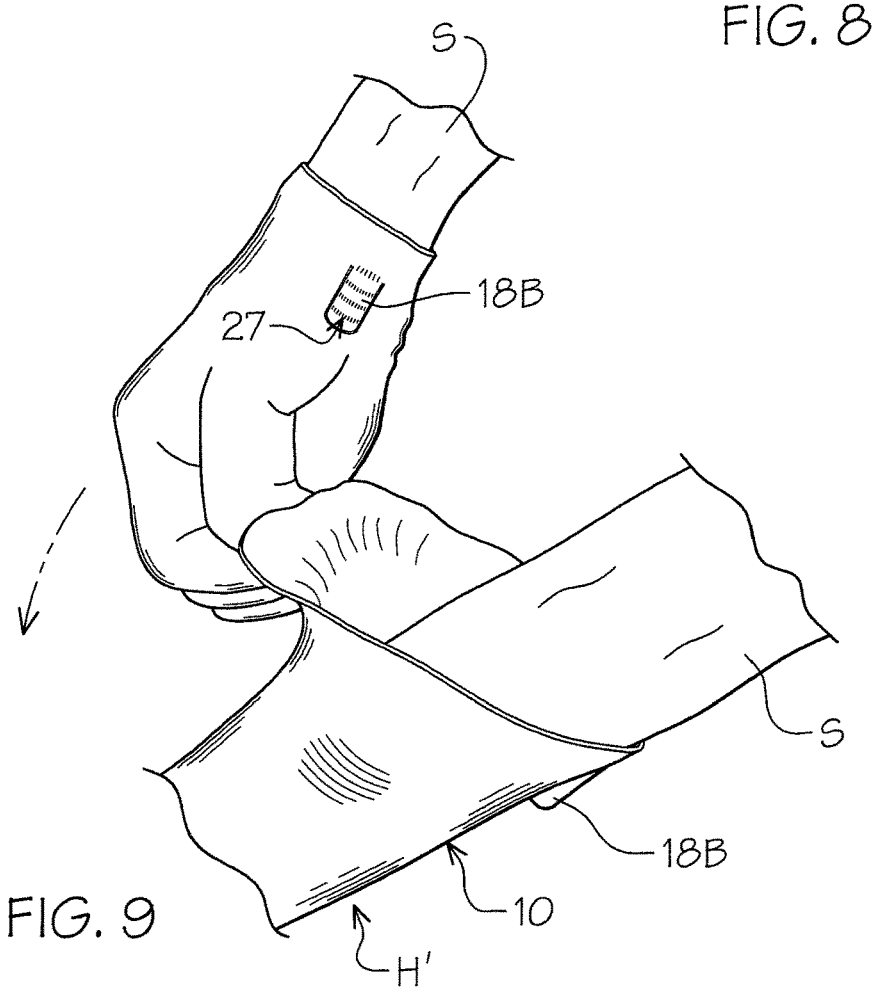
FIG. 9 is a perspective illustration of the glove hand engagement and removal action.

Accordingly, the finger tabs 18A and 18B formed on the mold representations 19A and 19B provide the orientation and positioning so that they are aligned respectively along the central longitudinal axial lines AL as illustrated in FIGS. 1 and 3 of the drawings with their positioning to afford ease of center end glove engagement required for removal as seen sequentially in FIGS. 8 and 9 of the drawings.

Figure 4:
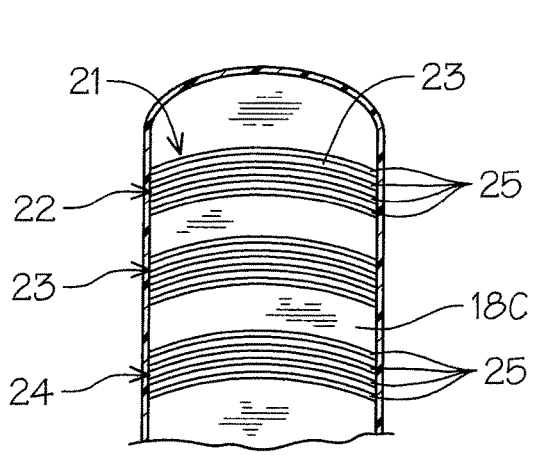
FIG. 4 is an enlarged partial sectional view of the finger tab showing multiple engagement ribs formed on its surface.
Figure 5:
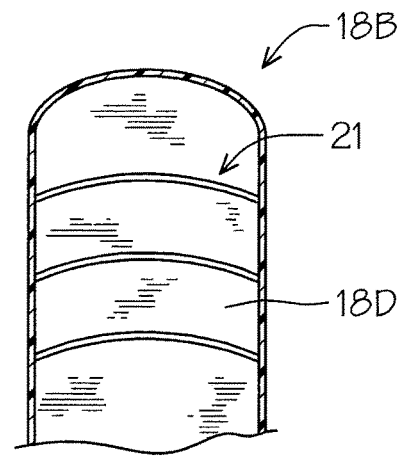
FIG. 5 is an enlarged partial sectional view of the finger tab showing oppositely disposed inner surface with engagement ribs thereon.
Figure 6:
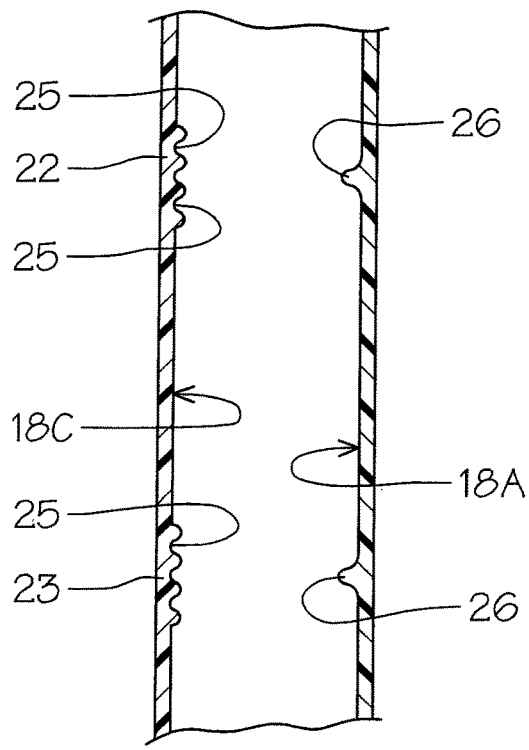
FIG. 6 is an enlarged sectional view of the interior surface of the finger tab showing the oppositely disposed aligned positioned ribs thereon.

The finger tabs 18A and 18B have a plurality of oppositely disposed interior ribs 21 formed on their respective effacing interior surfaces 18C and 18D in the foregoing distinctive arrangement as best seen in FIGS. 4 and 5 of the drawings.

Interlocking rib receiving sets 22, 23 and 24 extend transversely in longitudinally spaced relation to one another on the interior finger tab surface 18C. Each of the interlocking rib receiving sets 22-24 preferably has multiple parallel spaced contoured rib pairs forming corresponding number of receiving channels 25 there between.

The effacing inner finger tab surface 18D has in this embodiment spaced transverse extending insert ribs 26 each in alignment with the corresponding interlocking rib receiving sets 22-24.

Figure 7:
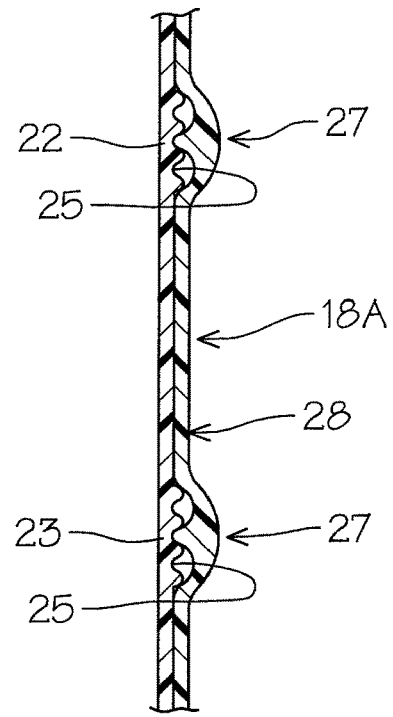
FIG. 7 is an enlarged sectional view of the finger tab with multiple ribs being engaged.

The insertion ribs 26 are of a greater upstanding dimension then that of the hereinbefore described opposing rib sets 22-24. Accordingly, the alignment of the rib receiving sets 22-24 and the insertion ribs 26 assure registerable engagement there between during use as illustrated in FIG. 7 of the drawings.

It will be evident from the above description that once the insertion rib 26 engagement occurs initiated by equilateral gripping of the finger tabs 18A and 18B by a user, a series of contoured raised transverse tactile bands 27 are formed on the exterior surface 28 of the respective finger tabs 18 providing enhanced assured grip when engaged.

Figure 10:
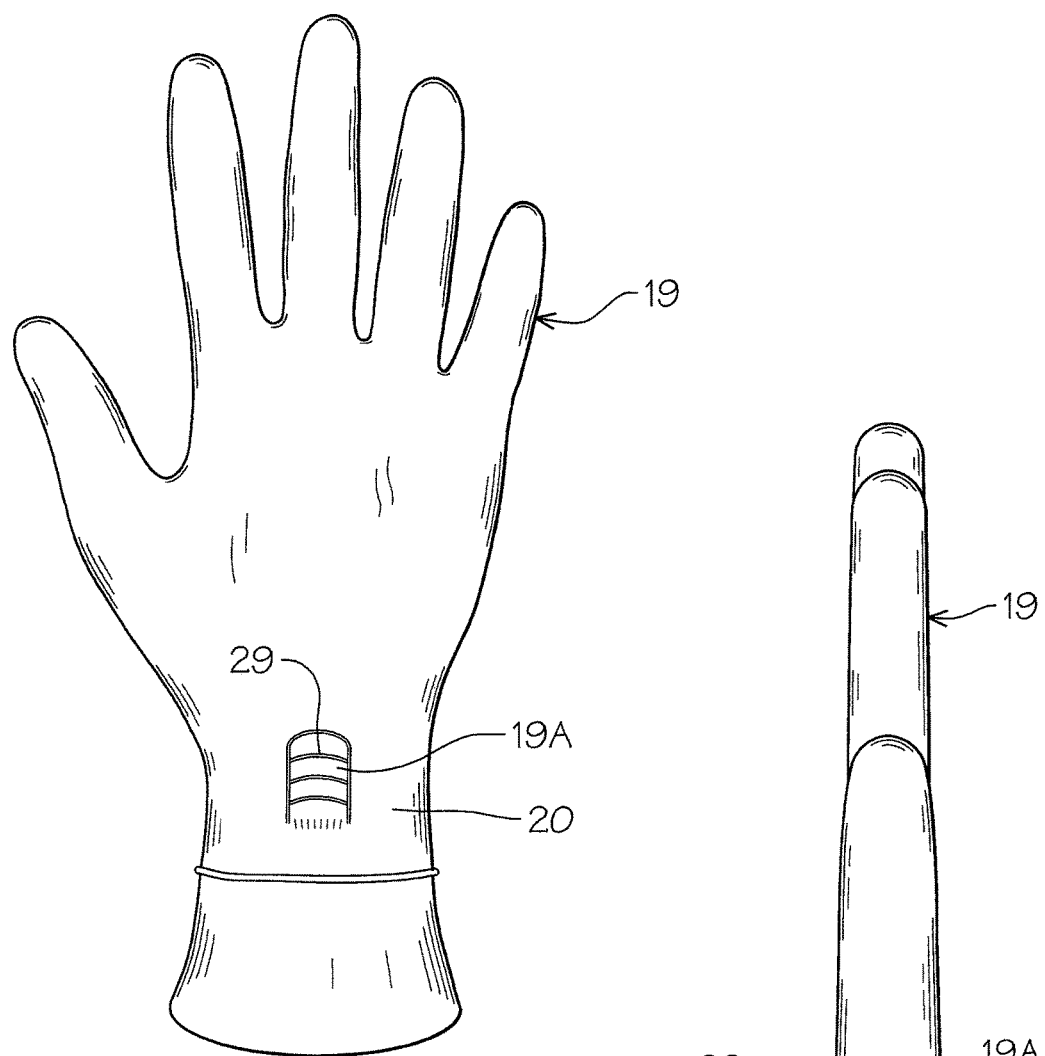
FIG. 10 is a front elevational view of a glove mold used to form the glove of the invention.
Figure 11:
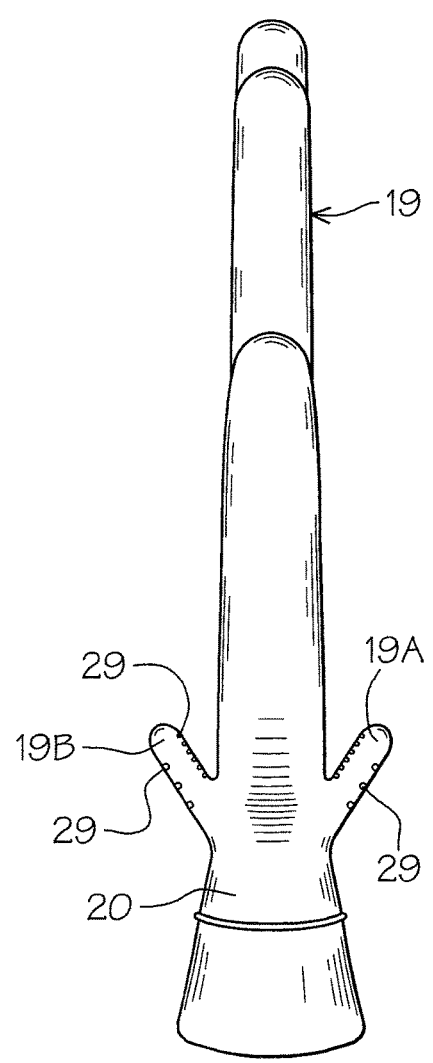
FIG. 11 is a side elevational view thereof.

The finger tab rib sets 22-24 and insertion rib 26 are formed by corresponding mold channels 29 on the hand mold 18 finger-like representations 19A and 19B shown enlarged for illustration and clarity in FIGS. 10 and 11 of the drawings. This allows for glove mold formation as is commercially available when used extensively in a manufacturing techniques and processes.

In use, the healthcare worker would wear the glove 10 and use it in a normal manner in the particular environment. To remove the glove 10, the healthcare worker, not shown, would grasp and pull the respective finger tab 18A with its now formed raised transverse bands 27 for enhanced grip, pulling the wrist portion 17 of the glove upwardly and away from the skin and then grasping the wrist portion 15 by insertion of their remaining gloved fingers of the same hand 14 under the glove as seen sequentially happening in FIGS. 8 and 9 of the drawings. The glove 10 is then pulled inside out and off the wearer's hand H' effectively isolating the contaminated outer surface. This removal action is in general accordance with the approved safe glove removal procedures recommended to minimize contamination during glove removal.

It will be seen that by use of the glove 10 removal finger tabs 18A and 18B which are ambidextrous assures a secure safe non-slip grip and a central point of contact pull engagement.

Given the ambidextrous nature of medical gloves in general and the oppositely disposed finger tabs 18A and 18B on the glove 10, it assures left or right hand first glove tab engagement and removal. The remaining glove H' shown in FIGS. 8 and 9 of the drawings is removed according to the recommended established removal without the required utilization of its remaining finger tabs 18A and 18B. This removal sequence prevents the wearer's skin S from being contaminated which is a primary goal to minimize spread of infection within the healthcare provider environment.

Referring back now to FIGS. 10 and 11 of the drawings, it will be seen that the gloves 10 of the invention can be made of any desirable material such as latex that will use the hereinbefore described modified hand mold 19 which has the addition of opposing finger tab molds 19A and 19B with the contoured relief rib forming channels 29 within. By utilization of an existing hand mold formation technology, the medical gloves can be made by commercially acceptable processes such as dipping or spraying common in the industry and well known to those skilled in the art.

It will thus be seen that a new and useful medical use orientated glove has been illustrated and described and that various changes and modification may be made thereto without departing from the spirit of the invention.

Therefore, I claim:

1. A glove to prevent contamination when removed, the glove comprising:
    a glove body member,
    a plurality of finger receiving elements extending from and in communication 5 with said glove body member,
    a wrist portion having an access opening, an enlarged lip extending about the access opening, finger tabs extending from the wrist portion in oppositely disposed relation to one another,
    a plurality of spaced parallel opposing ribs formed on respective effacing interior surfaces of said finger tabs,
    said opposing ribs aligned for interlocking registration with one another, multiple exterior raised surface bands on the finger tabs exterior surface defined by said interlocking ribs.

2. The glove set forth in claim 1 wherein said finger tabs are in spaced relation to said enlarged lip about said access opening.

3. The glove to prevent contamination when removed set forth in claim 1 wherein some of said spaced parallel ribs are in multiple parallel spaced sets on one of said interior surfaces.

4. The glove to prevent contamination when removed set forth in claim 1 wherein some of said spaced parallel opposing ribs are in singular parallel spaced relation to one another on one of said effacing interior surfaces of said finger tabs aligned for the selective locking registration there between.

5. The glove to prevent contamination when removed set forth in claim 1 wherein said raised bands on said finger tab's exterior surface are in spaced parallel relation to one another extending transversely across the finger tabs exterior surface.

6. The glove to prevent contamination when removed set forth in claim 1 wherein said respective finger tabs are of a length and width less than that of the known dimension of the finger receiving elements from said glove body member.

7. The glove to prevent contamination when removed set forth in claim 1 wherein said glove is made of flexible thin synthetic resin material on a glove hand mold.

8. The glove to prevent contamination set forth in claim 7 wherein said glove hand mold comprises;
    multiple finger and single thumb mold extensions,
    a pair of oppositely disposed extra finger-like mold representations extending therefrom,
    molding channels on said finger-like mold representations in oppositely disposed relation to one another thereon.

* * * * *